United States Patent
Comeau et al.

(10) Patent No.: US 11,577,283 B2
(45) Date of Patent: Feb. 14, 2023

(54) MATTRESS CLEANING SYSTEM

(71) Applicant: MATTRESS SPA INC., Winnipeg (CA)

(72) Inventors: Robert Comeau, Winnipeg (CA); Robert Amborsky, Winnipeg (CA)

(73) Assignee: Mattress Spa Inc., Manitoba (CA)

( * ) Notice: Subject to any disclaimer, the term of this patent is extended or adjusted under 35 U.S.C. 154(b) by 52 days.

(21) Appl. No.: 16/613,954

(22) PCT Filed: May 29, 2018

(86) PCT No.: PCT/CA2018/050624
§ 371 (c)(1),
(2) Date: Nov. 15, 2019

(87) PCT Pub. No.: WO2018/223219
PCT Pub. Date: Dec. 13, 2018

(65) Prior Publication Data
US 2021/0316339 A1    Oct. 14, 2021

Related U.S. Application Data

(60) Provisional application No. 62/517,286, filed on Jun. 9, 2017.

(51) Int. Cl.
*B08B 3/10* (2006.01)
*D06G 1/00* (2006.01)
*B08B 3/02* (2006.01)

(52) U.S. Cl.
CPC ................. *B08B 3/10* (2013.01); *B08B 3/02* (2013.01); *D06G 1/00* (2013.01); *B08B 2203/0211* (2013.01); *D10B 2505/08* (2013.01)

(58) Field of Classification Search
CPC ..... B08B 3/10; B08B 3/02; B08B 2203/0211; D06G 1/00; D10B 2505/08;
(Continued)

(56) References Cited

U.S. PATENT DOCUMENTS 3,482,931 A * 12/1969 Hallstrom ............... A61L 2/22
134/115 R
3,789,228 A * 1/1974 Bouchard ............... A61L 2/10
250/492.1

(Continued)

FOREIGN PATENT DOCUMENTS

DE          1920307       11/1970
DE       102005025592    10/2006
(Continued)

*Primary Examiner* — Benjamin L Osterhout
(74) *Attorney, Agent, or Firm* — Ryan W. Dupuis; Kyle R. Satterthwaite; Ade & Company Inc.

(57) ABSTRACT

A mattress cleaning system receives a mattress in a tank of wash liquid so that the mattress is fully submerged. A pressure applicator, for example a mechanical structure or a jetted flow of wash fluid, applies a cyclical compressive force to the sleeping surface of the mattress while the mattress is fully submerged so as to cause flushing of the wash liquid outwardly of the mattress through at least the sleeping surface of the mattress. When using a barrier to isolate one of the surfaces of the mattress on a first side of the barrier from remaining surfaces of the mattress on a second side of the barrier, use of a blower to create an air pressure differential between opposing sides of the barrier causes migration of the wash liquid through the mattress from the isolated surface of the mattress to the remaining surfaces for drying the mattress.

21 Claims, 10 Drawing Sheets

(58) Field of Classification Search
CPC .... A61L 2202/15; A61L 2/10; A61L 2202/17; A61L 2/07; A61L 2/183; A61L 2/202; A61L 2/04; A61L 2202/26
See application file for complete search history.

(56) References Cited

U.S. PATENT DOCUMENTS

| | | | | |
|---|---|---|---|---|
| 2005/0201910 | A1* | 9/2005 | Shou | A61L 2/10 422/186 |
| 2011/0094681 | A1* | 4/2011 | Bisges | A61L 2/14 156/345.1 |
| 2013/0037063 | A1* | 2/2013 | King | A61L 2/07 134/109 |
| 2013/0117959 | A1* | 5/2013 | Stryker | A47L 11/00 15/319 |
| 2013/0263496 | A1* | 10/2013 | Maloney | A61L 2/04 43/132.1 |
| 2014/0000648 | A1* | 1/2014 | Ingle | A61L 2/04 134/1 |
| 2014/0137330 | A1* | 5/2014 | Lisi | A47C 21/044 5/694 |
| 2015/0376831 | A1* | 12/2015 | Ingle | A61L 2/04 68/5 D |

FOREIGN PATENT DOCUMENTS

| | | |
|---|---|---|
| EP | 0157252 | 10/1985 |
| EP | 0634514 | 1/1995 |
| JP | 03213185 | 9/1991 |
| JP | 2006296748 | 11/2006 |
| JP | 2013071048 | 4/2013 |
| KR | 20-0285797 | 8/2002 |

* cited by examiner

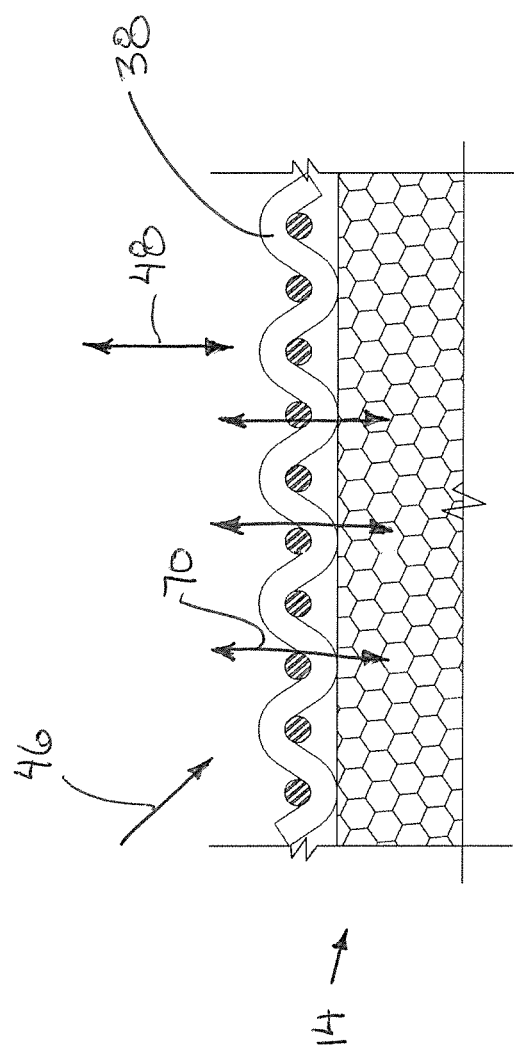

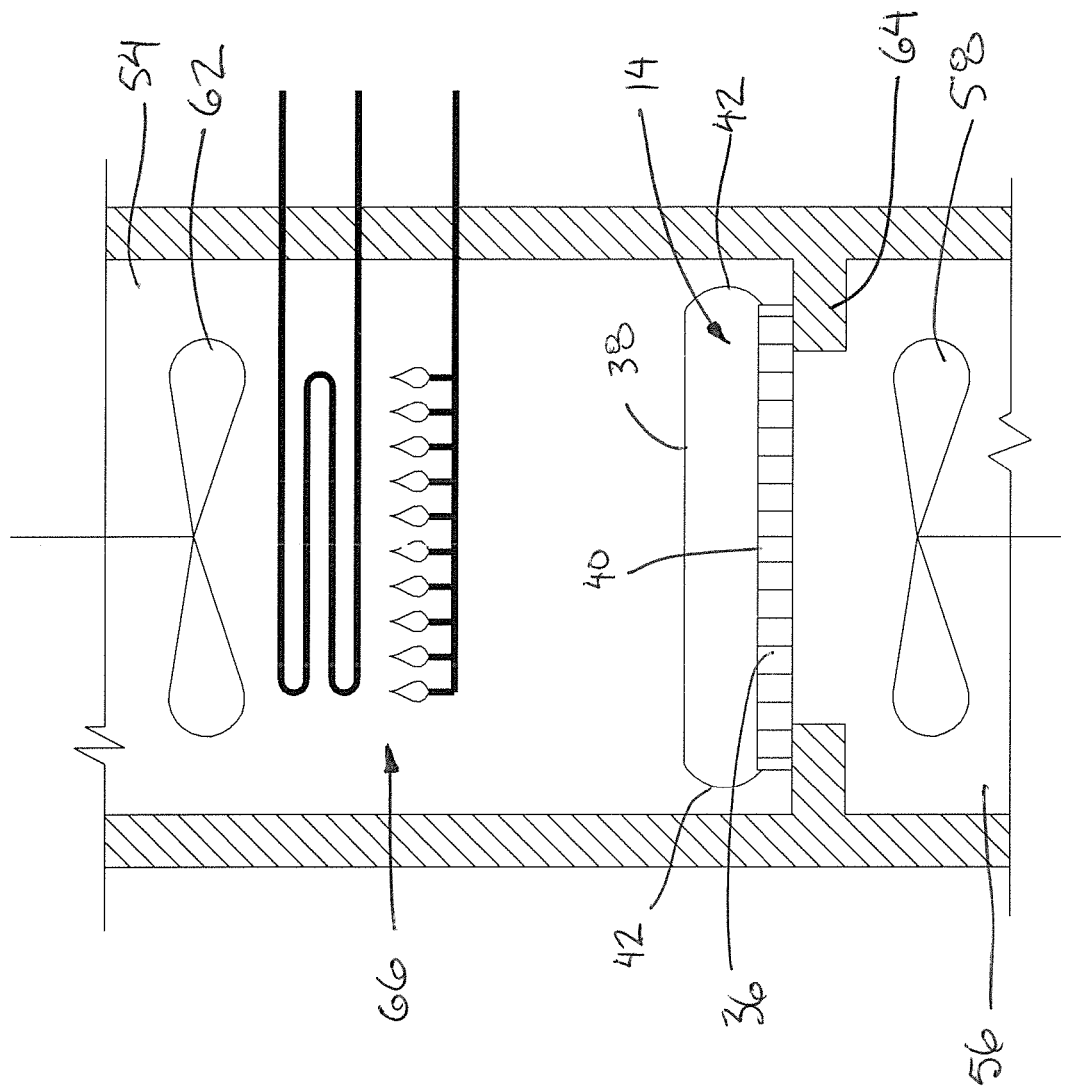

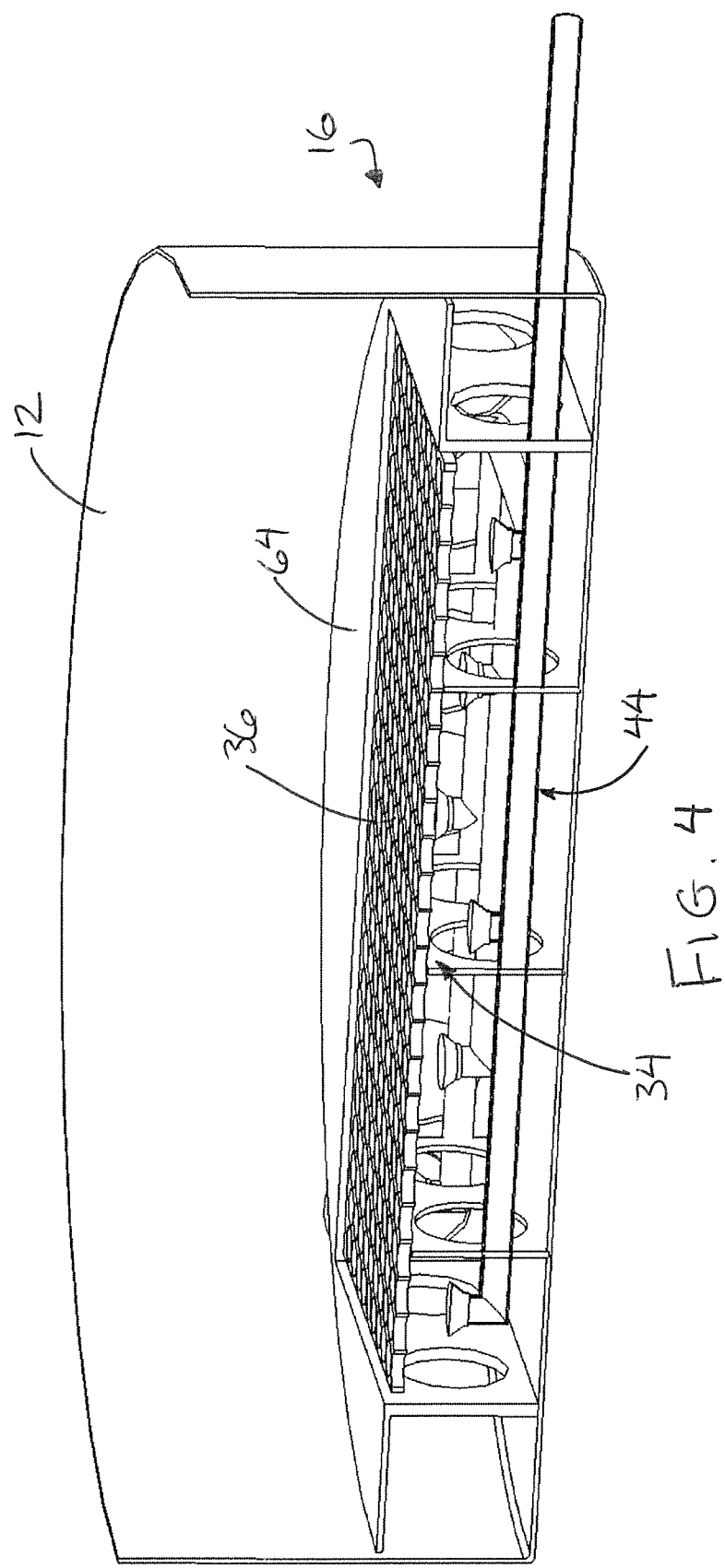

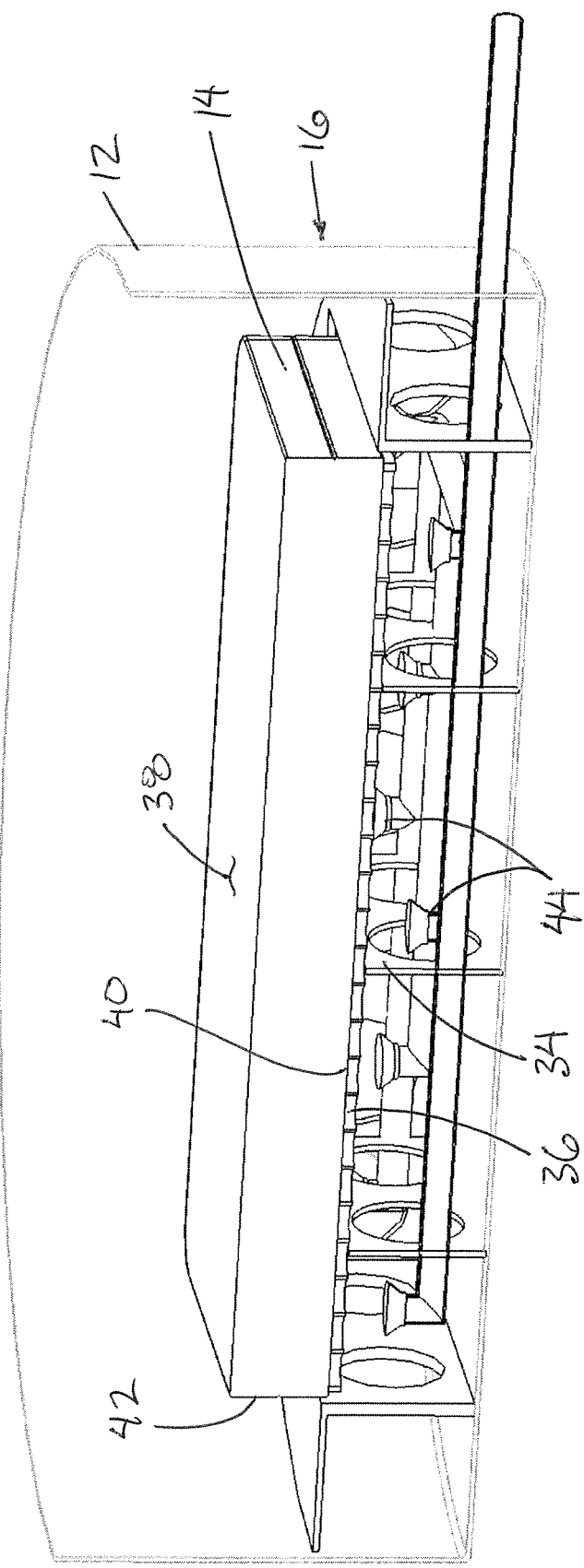

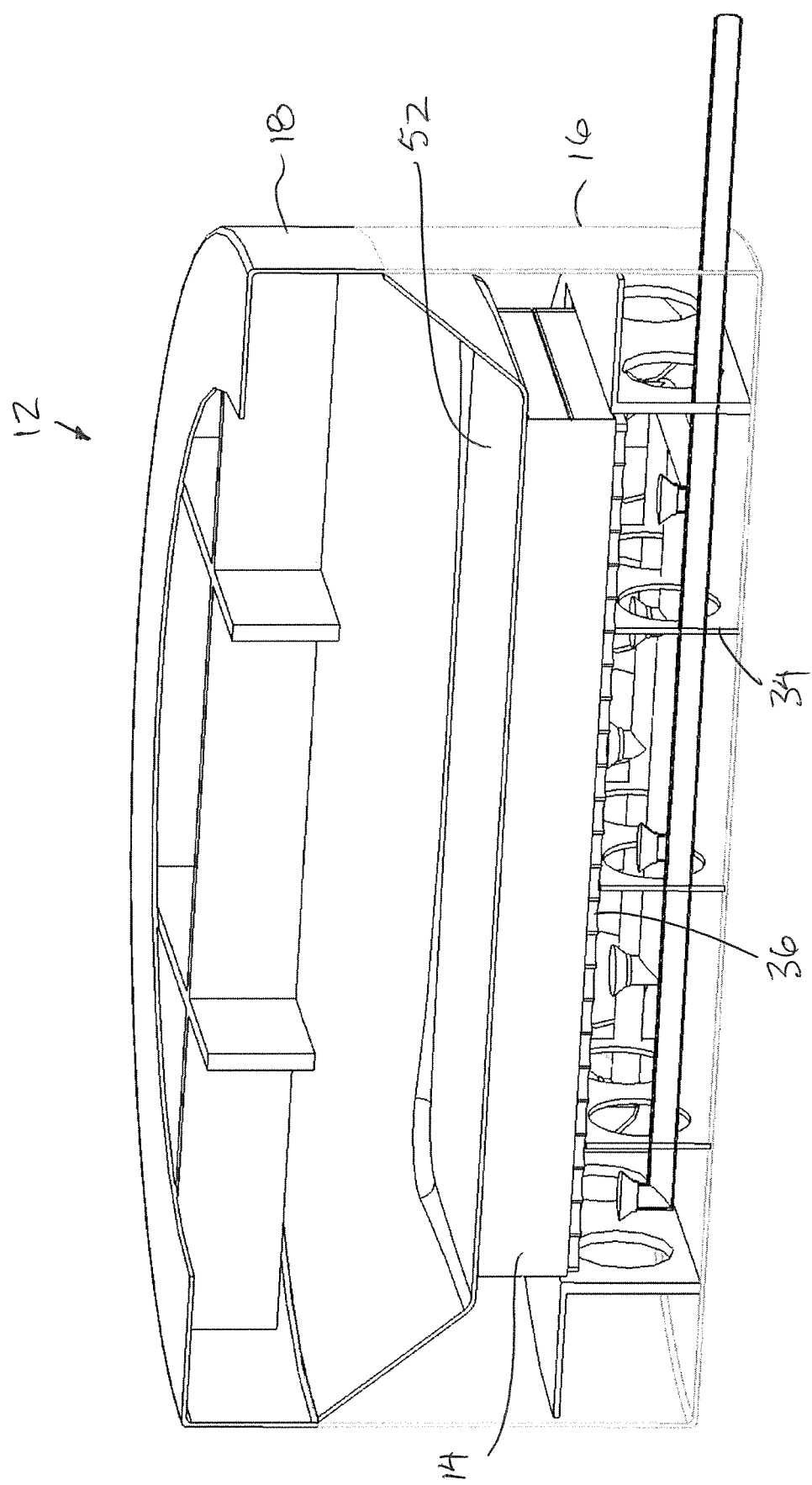

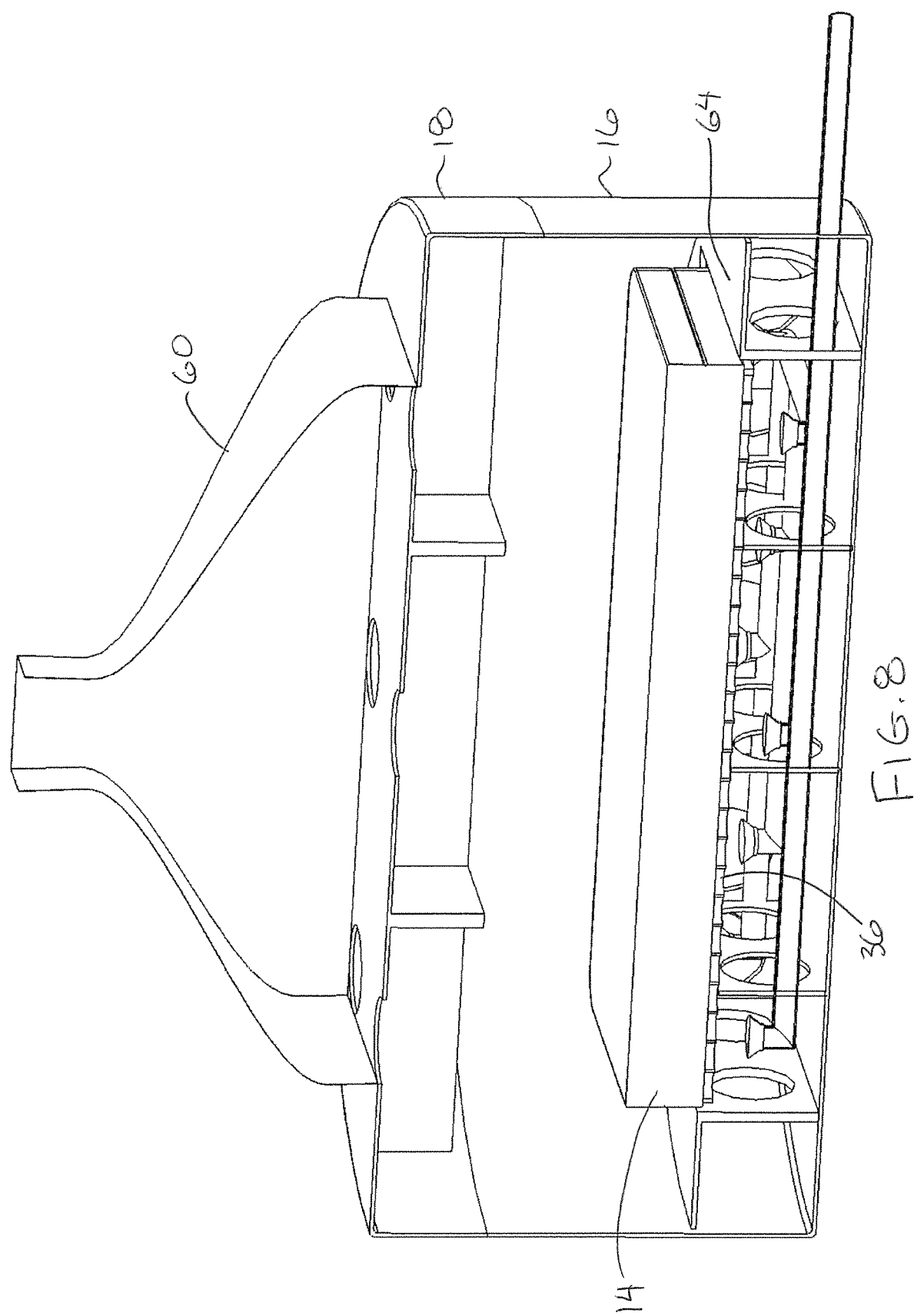

MATTRESS CLEANING SYSTEM

This application claims priority benefit to U.S. provisional application Ser. No. 62/517,286, filed Jun. 9, 2017.

FIELD OF THE INVENTION

The present invention relates to a system for cleaning a mattress including a washing step in which the mattress is submerged in a wash liquid and a drying step in which the mattress is dried using an air pressure differential applied to different surfaces of the mattress to cause migration of any remaining wash liquid externally of the mattress.

BACKGROUND

Modern mattresses for sleeping upon have typically become a complex structure involving many different layers of material to accommodate different user preferences for comfort. As a result of the increasing complexity of the mattress structure, it is often recommended that a mattress be disposed of when it has become soiled by anything more than a superficial stain. Any attempt to wash a mattress to clean the mattress beyond superficial staining can lead to penetration of wash liquids or soiling materials deeper into the mattress into inaccessible cavities which are difficult to access and thus prone to problems such as mold.

SUMMARY OF THE INVENTION

According to one aspect of the invention there is provided a mattress cleaning system for cleaning a mattress comprising a sleeping surface for supporting a user thereon, a backside surface opposite the sleeping surface, and a plurality of side surfaces connected between the sleeping surface and the backside surface about a perimeter of the mattress, the system comprising:

a tank arranged to receive the mattress and a wash liquid therein;

a mattress support arranged to receive the mattress supported thereon such that the mattress is fully submerged in the wash liquid in the tank; and a pressure applicator adapted to apply a cyclical compressive force to the sleeping surface of the mattress while the mattress is supported on the mattress support fully submerged within the tank so as to cause flushing of the wash liquid outwardly of the mattress through at least the sleeping surface of the mattress.

According to another aspect of the present invention there may further be provided a method of cleaning a mattress comprising a sleeping surface for supporting a user thereon, a backside surface opposite the sleeping surface, and a plurality of side surfaces connected between the sleeping surface and the backside surface about a perimeter of the mattress, the method comprising:

providing a tank;

supporting the mattress in the tank such that the mattress is fully submerged in the wash liquid in the tank; and cyclically applying a compressive force to the sleeping surface of the mattress while the mattress is fully submerged within the tank so as to cause flushing of the wash liquid outwardly of the mattress through at least the sleeping surface of the mattress.

Use of a system to apply a cyclical compressive force while a mattress is submerged for flushing liquid outwardly through the surfaces of the mattress can dislodge soiling materials from the mattress without penetrating the soiling materials further into the cavities of the mattress.

The pressure applicator may include at least one jet nozzle adapted to direct a jet of wash liquid onto the sleeping surface of the mattress in the tank. Said at least one jet nozzle may be supported relative to the tank so as to be arranged to direct the jet of wash liquid non-perpendicularly to the sleeping surface in a sweeping motion displaced across the sleeping surface of the mattress.

The pressure applicator may also include (i) a grate supported in the tank so as to receive the mattress between the mattress support and the grate in which the grate is adapted to allow flow of wash liquid therethrough and (ii) a drive arrangement for reciprocating the grate relative to the mattress support between a first position at a first spacing from the mattress support and a second position at a second spacing less than the first spacing from the mattress support for compressing the mattress as the grate is displaced from the first position to the second position.

Preferably the first spacing and the second spacing are adjustable amounts.

Preferably the grate is arranged to fully span the mattress.

The drive arrangement is preferably adapted to displace the grate from the first position to the second position at a greater speed than from the second position to the first position.

When the mattress support comprises a grate arranged to receive the backside surface of the mattress thereon and being adapted to allow flow of wash liquid therethrough, the compressive force may be applied by the pressure applicator so as to cause flushing of the wash liquid outwardly of the mattress through the backside surface of the mattress.

The system preferably further includes a drain for draining the wash liquid from the tank, and a blower in communication with the tank for drying the mattress while the mattress remains supported within the tank.

The system described above may further include a mattress drying system operable within the wash tank in which the mattress drying system comprises: (i) a barrier arranged to isolate at least one of the surfaces of the mattress from remaining ones of the surfaces of the mattress; and (ii) a blower arranged to create an air pressure differential between a first side of the barrier and a second side of the barrier so as to cause migration of wash liquid through the mattress from the at least one isolated surface of the mattress to the remaining surfaces of the mattress.

According to another important independent aspect of the present invention there is provided a mattress cleaning system for cleaning a mattress comprising a sleeping surface for supporting a user thereon, a backside surface opposite the sleeping surface, and a plurality of side surfaces connected between the sleeping surface and the backside surface about a perimeter of the mattress, the system comprising:

a wash tank arranged to receive the mattress and a wash liquid therein for washing the mattress; and a mattress drying system comprising:

a barrier arranged to isolate at least one of the surfaces of the mattress on a first side of the barrier from remaining ones of the surfaces of the mattress on a second side of the barrier; and a blower arranged to create an air pressure differential between the first side of the barrier and the second side of the barrier so as to cause migration of wash liquid through the mattress from the at least one isolated surface of the mattress to the remaining surfaces of the mattress.

The use of a barrier and blower to create an air pressure differential can cause the mattress to be initially compressed while the pores of the mattress remain full of wash liquid so that the squeezing of the mattress can assist in dewatering of the mattress. Continued air pressure differential as the mattress becomes dryer will cause a flow of drying air to pass fully through the mattress and remove any remaining undesirable moisture from the mattress.

The mattress drying system may further comprise (i) a press including a first pressing surface for engaging the backside surface of the mattress, (ii) a second pressing surface for engaging the sleeping surface of the mattress, and (iii) a press drive arrangement arranged to displace the second pressing surface relative to the first pressing surface to compress the mattress subsequent to washing of the mattress.

The barrier is preferably adapted to isolate the backside surface of the mattress from the sleeping surface of the mattress.

The barrier may be substantially coplanar with and surrounding a grate adapted to span the backside of the mattress and support the mattress thereon.

The barrier may also be arranged to cover the side surfaces of the mattress.

Alternatively, the barrier may be adapted to isolate the side surfaces of the mattress on the first side of the barrier from the backside surface and the sleeping surface on the second side of the barrier.

The system may further include a controller operatively connected to the blower so as to be adapted to pulse operate the blower.

According to another aspect of the present invention there is provided a method of cleaning a mattress comprising a sleeping surface for supporting a user thereon, a backside surface opposite the sleeping surface, and a plurality of side surfaces connected between the sleeping surface and the backside surface about a perimeter of the mattress, the method comprising:

washing the mattress in a tank using a wash liquid; and using a barrier to isolate at least one of the surfaces of the mattress on a first side of the barrier from remaining ones of the surfaces of the mattress on a second side of the barrier; and using a blower to create an air pressure differential between the first side of the barrier and the second side of the barrier so as to cause migration of the wash liquid through the mattress from the at least one isolated surface of the mattress to the remaining surfaces of the mattress.

The method may further include using the blower to create a sufficiently large air pressure differential between the first side and the second side of the barrier to at least partially compress the mattress.

BRIEF DESCRIPTION OF THE DRAWINGS

Some embodiments of the invention will now be described in conjunction with the accompanying drawings in which:

FIG. 2 is a schematic representation of the flushing action occurring during the washing cycle of the mattress cleaning system;

FIG. 3 is a schematic representation of the air pressure differential created between different services of the mattress during the drying cycle of the mattress cleaning system;

FIG. 4 is a partly sectional view of the wash tank of the mattress cleaning system prior to receiving a mattress therein;

FIG. 5 is a partly sectional view of the wash tank upon receiving the mattress therein;

FIG. 7 is a partly sectional view of the wash tank illustrating a bladder member for compressing the mattress for dewatering subsequent to the wash cycle;

FIG. 8 is a partly sectional view of the wash tank in connection with suitable ducting to apply an air pressure differential to different surfaces of the mattress during the drying cycle.

In the drawings like characters of reference indicate corresponding parts in the different figures.

DETAILED DESCRIPTION

Figure 1:
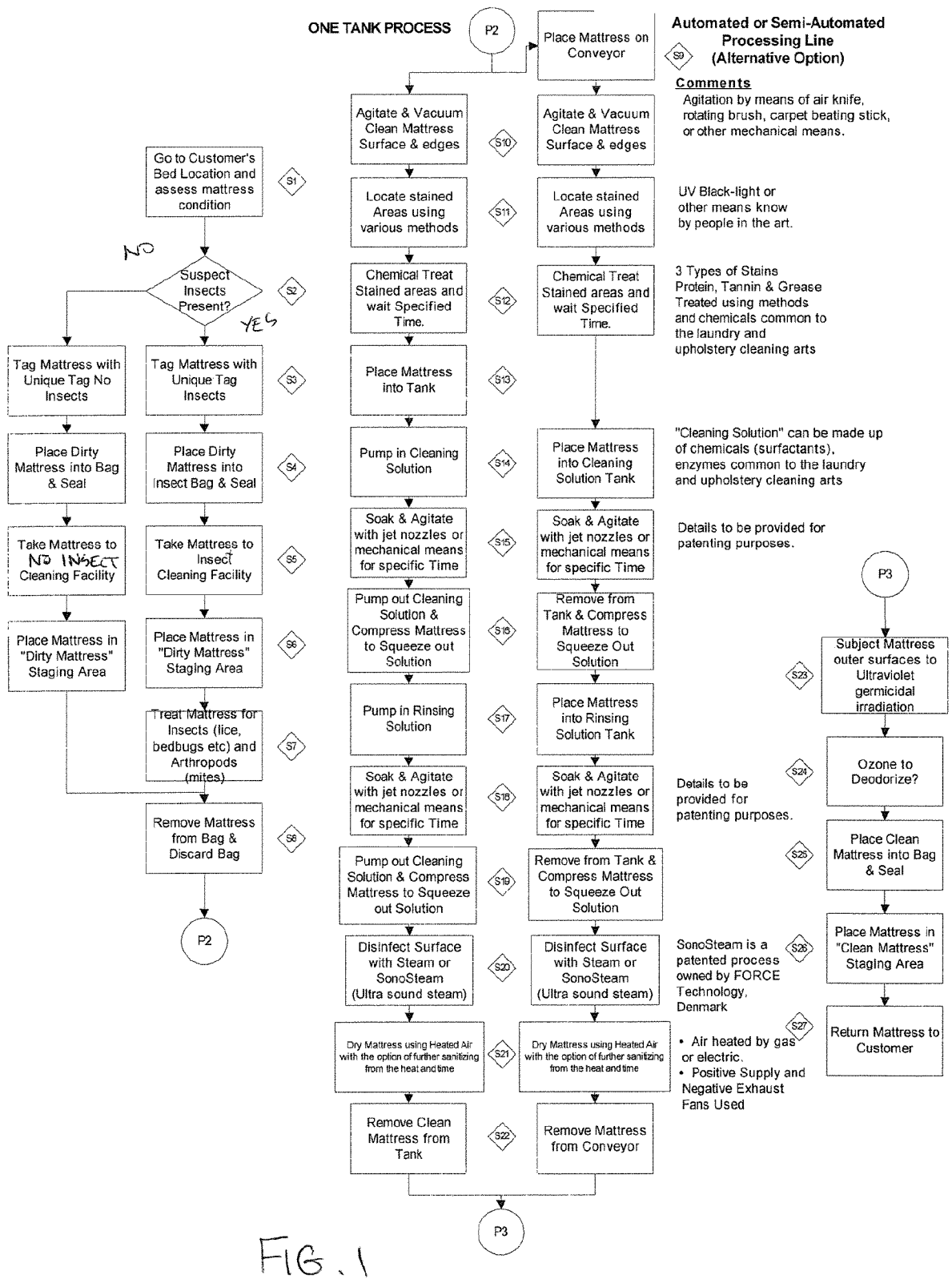
FIG. 1 is a flow chart representing the various options for executing the method of washing and drying a mattress according to the mattress cleaning system of the present invention.
Figure 6A:
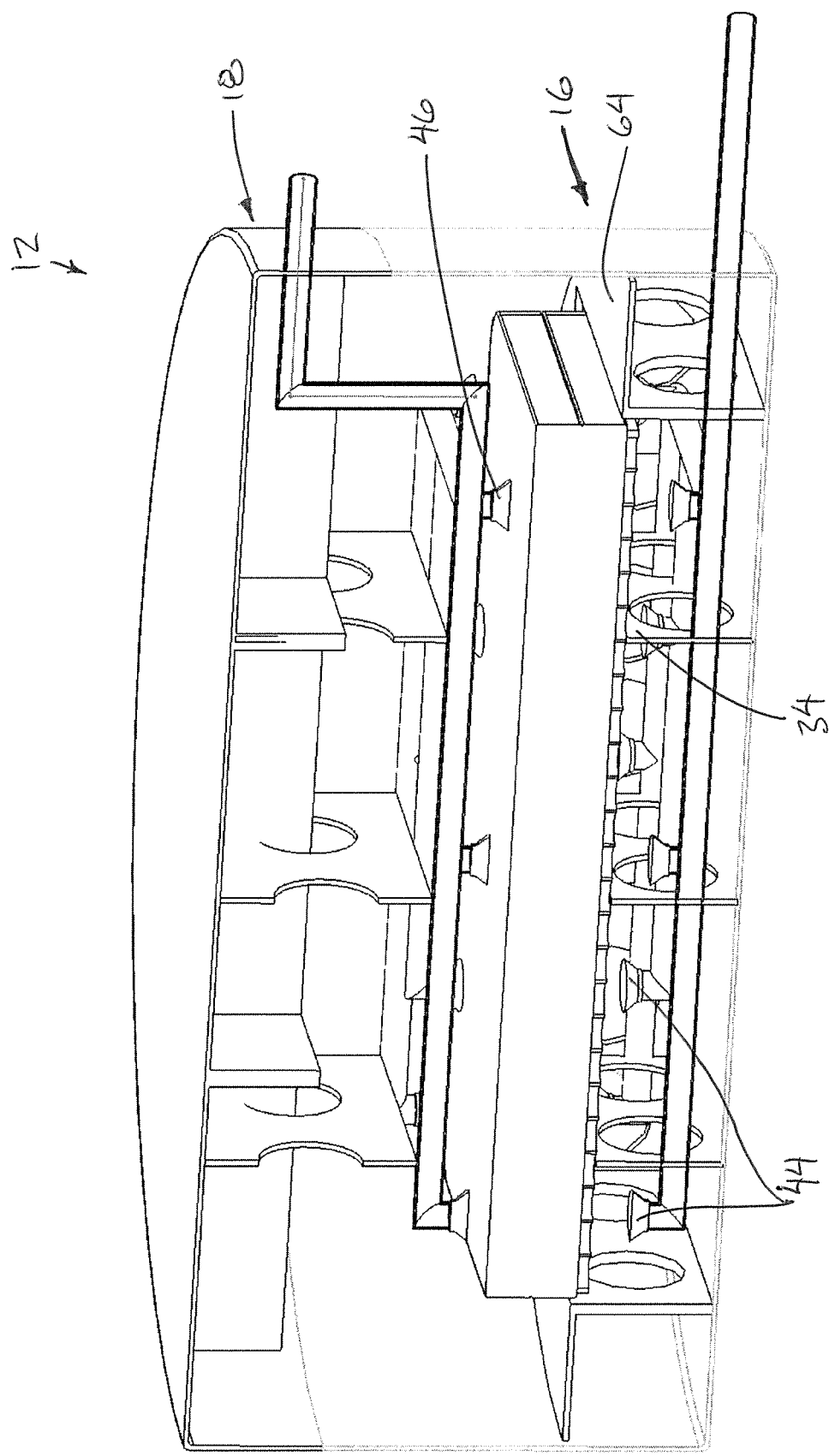
FIG. 6A is a partly sectional view of the wash tank using a series of nozzle to apply jets of wash liquid to the mattress for cyclically compressing surfaces of the mattress to be cleaned during the wash cycle.
Figure 6B:
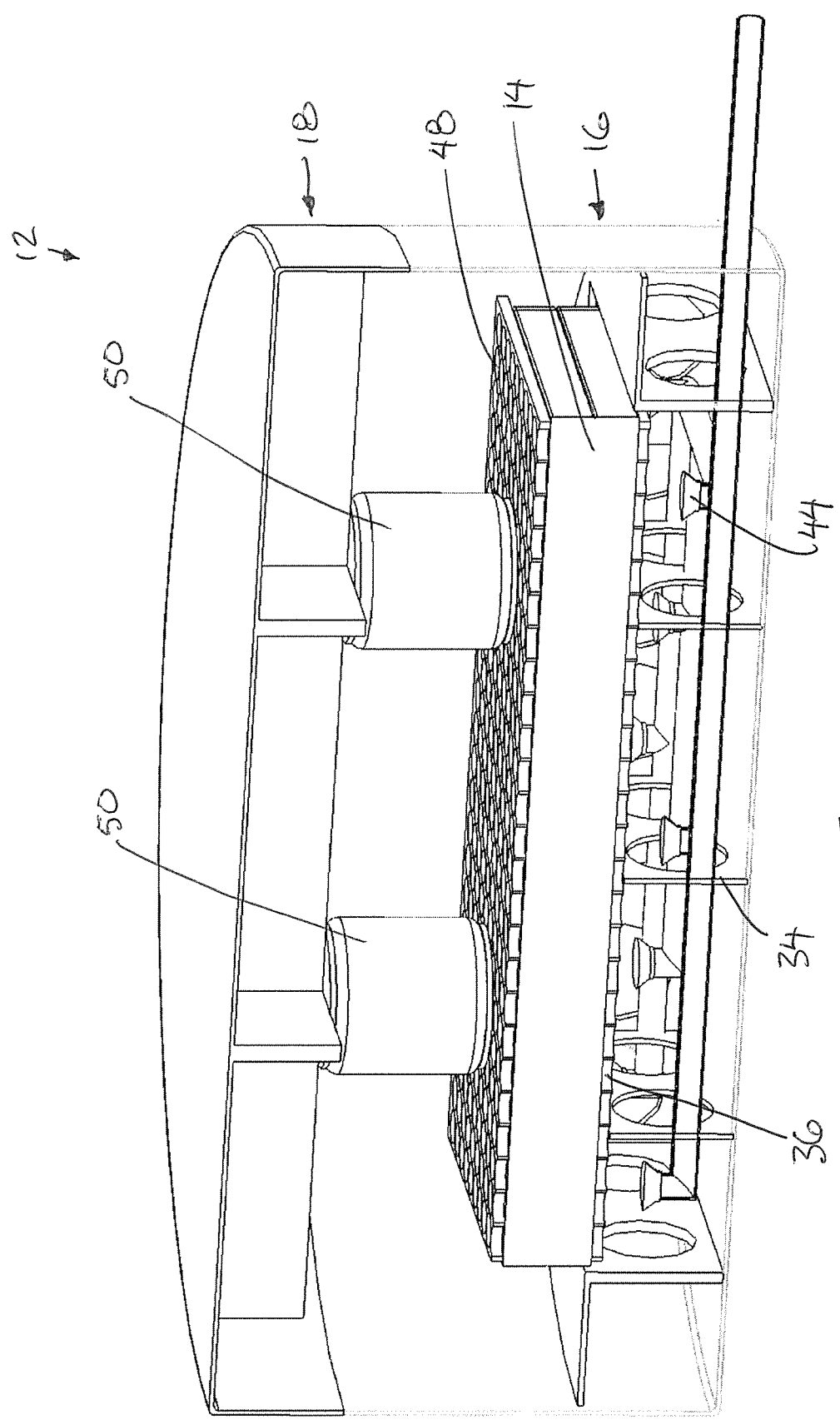
FIG. 6B is a partly sectional view of the wash tank using a grate to cyclically compress surfaces of the mattress to be cleaned during the wash cycle, for use in place of or in addition to the nozzle according to FIG. 6A, in which the grate may also be used for dewatering subsequent to the wash cycle.

Referring to the accompanying figures there is illustrated a mattress cleaning system generally indicated by reference numeral 10. The system is adapted to clean a mattress by subjecting the mattress to various cycles including one or more wash cycles, one or more rinse cycles, a drying cycle, and optionally one or more treatment cycles.

The system 10 typically includes a wash tank 12 adapted to receive a mattress 14 therein and to contain wash liquid therein such that the mattress can be fully submerged during a wash cycle within the wash tank. As illustrated, the tank includes a lower tank portion 16 having a floor and upright side walls to define a vessel for containing the wash liquid therein, and an upper tank portion 18 forming a lid which is movably supported relative to the lower tank portion between open and closed positions for washing or drying the mattress when closed and for loading or unloading a mattress from the tank when open. A plurality of different upper tank portions may be provided which are interchangeable upon the lower tank portion to perform the various functions described herein.

A wash liquid supply tank 20 and a rinse liquid supply tank 22, and optionally various additional treatment tanks, are typically located in proximity to the wash tank within a common mattress cleaning facility. Supply piping 24 communicates from the supply tanks to the wash tank with respective valves 26 in series therewith to open and close communication of the various supply tanks with the wash tank. One or more supply pumps 28 are also connected in series with the supply piping to pump liquid from the supply tanks into the wash tank when actuated. One or more drain ports are also provided in the bottom of the wash tank in communication with return piping 30 which communicates from the wash tank back to the supply tanks for recycling liquids or to an optional disposal drain for disposing of spent liquids. A return pump 32 in series with the return piping assists in directing the flow of liquid through the wash tank. In this manner, during a wash cycle, the supply and return pipes may be operated such that a flow of liquid from one of the supply tanks is cycled to the wash tank and back to the supply tank. The same liquid may be reused for multiple wash cycles for one or more mattresses for example, but once the liquid is considered no longer effective for further wash cycles the liquid can be replaced in the corresponding supply tank.

A suitable mattress support 34 is supported within the lower portion 16 of the wash tank for supporting the mattress during the wash cycle and optionally through other cycles involved in cleaning the mattress. More specifically the mattress support is adapted to support the mattress such that it is fully submerged and such that there is a liquid space fully surrounding all sides of the mattress during the wash cycle so that circulating liquid in the wash tank is well-suited to come in contact with and wash all surfaces of the mattress. In the illustrated embodiment, the mattress support comprises a horizontal lower grate 36 comprising a rigid mesh having a plurality of openings therein which readily allows the flow of wash liquid therethrough.

A typical mattress 14 for use with the present invention includes a top sleeping surface 38 which fully spans a top side of the mattress, a backside surface 40 fully spanning the bottom side of the mattress opposite the sleeping surface 38, and a plurality of side surfaces 42 extending about the full perimeter of the mattress and spanning the full height of the mattress between the backside surface at the bottom and the sleeping surface at the top. In the instance of a reversible mattress, the backside surface of the mattress is a second sleeping surface similar in configuration to the top sleeping surface 38.

To assist in executing the wash cycle, an array of first nozzles 44 are supported within the lower portion of the wash tank below the grate 36 of the mattress support. The first nozzles 44 are directed upwardly for directing jets of liquid onto the backside surface 40 of the mattress supported on the upper supporting surface of the lower grate 36 of the mattress support by directing liquid upwardly through the openings in the lower grate.

An array of second nozzles 46 are also supported within the wash tank above the grate, spaced thereabove by a suitable distance to receive the mattress between the second nozzles 46 and the grate. The second nozzles 46 are directed downwardly for directing jets of liquid onto the top sleeping surface of the mattress which is supported on the lower grate 36. The second nozzles 46 are typically supported to be removable from the wash tank together with the upper portion 18 of the tank to provide access for loading and unloading a mattress into the tank.

All of the nozzles are typically mounted to allow some movement relative to the mattress support. This can be accomplished by supporting the nozzles to be rotated, translated, or swept through various ranges of motion such that the pressurized jets of liquid generated from the nozzles are directed non-perpendicularly onto corresponding surfaces of the mattress in a pulsing or sweeping manner relative to the mattress surfaces. The nozzles are supplied with liquid flow under pressure from the supply pump to produce the pressurized liquid jets directed onto the mattress.

In the illustrated embodiment, an upper grate 48 is also supported within the wash tank for engaging the top sleeping surface of the mattress opposite the backside 40 supported on the lower grate 36. The upper grate also comprises a rigid mesh having a plurality of openings therein to allow liquid flow to pass readily through the grate. The upper grate may be supported in the tank by the upper portion 18 of the tank such that the upper grate is also readily removable from the tank together with the upper portion for loading and unloading a mattress.

A drive arrangement supports the upper grate to reciprocate relative to the lower grate for cyclically compressing and releasing the mattress during a wash cycle, during a rinse cycle, or during a dewatering cycle prior to drying the mattress. More particularly the drive arrangement may comprise a pair of linear actuators operable to be extended and retracted such that the upper grate is displaced between a first position at a first spacing from the lower grate to receive the mattress therebetween without compression, and a second position at a second spacing less than the first spacing so as to cause the mattress therebetween to be compressed in height.

As shown in FIG. 7, the wash tank may also be provided with a bladder membrane 52 arranged to fully span over one side of the mattress opposite the lower grate. The bladder membrane 52 fully spans across the tank to isolate an upper portion of the tank above the membrane 52 from a lower portion of the tank below the membrane 52. By applying a pressure differential between the upper and lower parts of the tank, that is by providing a greater pressure using air in the bladder chamber above the membrane or vacuum in the chamber below the membrane, the bladder membrane will apply an even compressive force to the top side of the mattress for compressing the mattress between the bladder membrane and the lower grate to assist in dewatering the mattress prior to a drying cycle. The bladder membrane may also be supported relative to an upper portion 18 of the wash tank to be removable with the upper portion of the wash tank from the lower portion of the wash tank during loading and unloading of the mattress.

Figure 9:
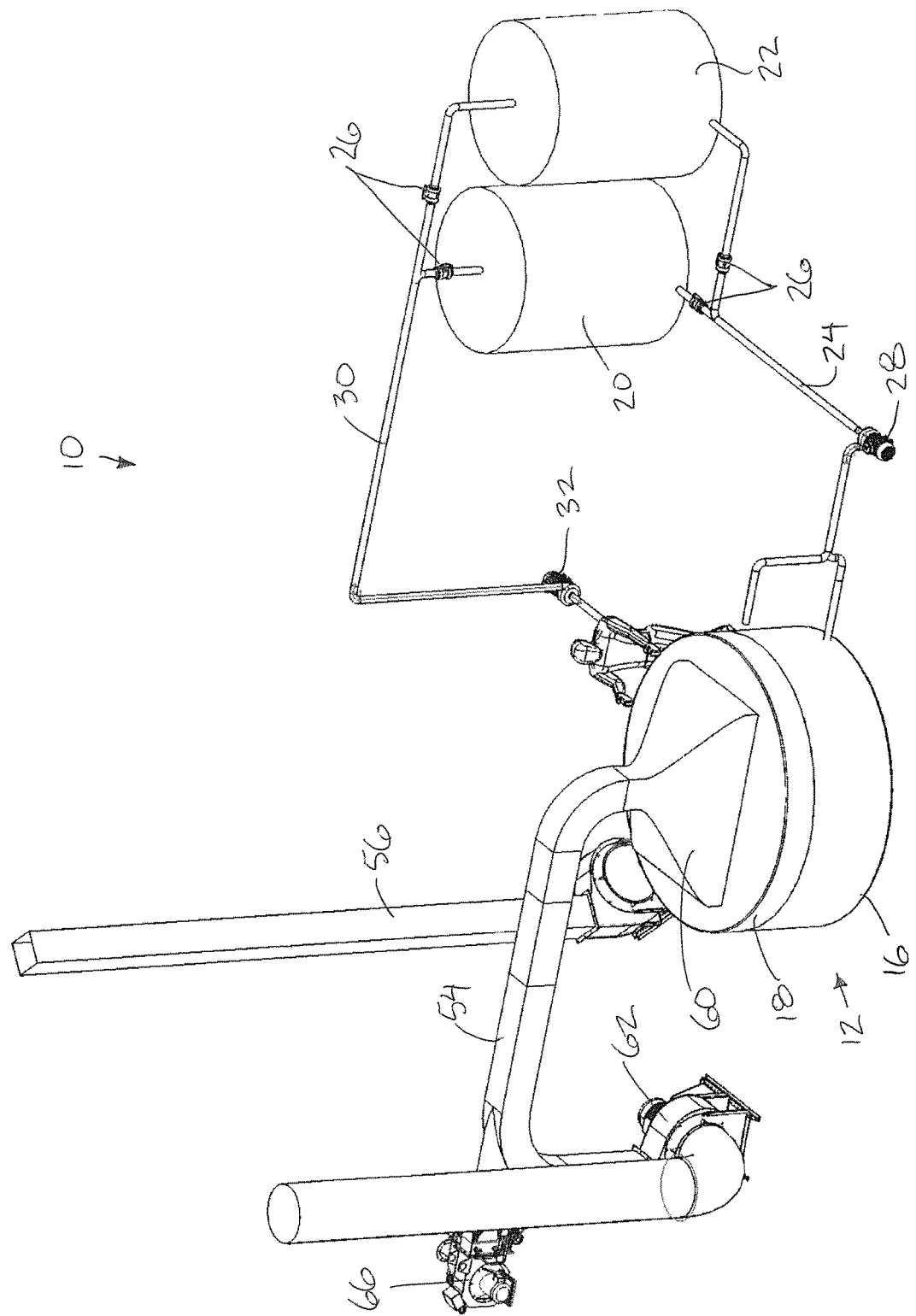
FIG. 9 is a schematic representation of the overall mattress cleaning system including an auxiliary tank for supplying washing and rinsing liquids to the wash tank, and one or more blowers to create the air pressure differential across different surfaces of the mattress during the drying cycle.

The drying of the mattress occurs by selectively connecting inlet ducting 54 and exhaust ducting 56 to the wash tank 12 as best illustrated in FIG. 9. The exhaust ducting 56 typically communicates with the wash tank through a suitable gate in the wall of the wash tank which can be operated between open and closed positions for drying and washing cycles respectively. A suitable exhaust fan 58 is coupled to the exhaust ducting 56 so as to be operable to draw air out of the tank and produce a vacuum pressure in the lower portion of the tank. The supply ducting 54 in the illustrated embodiment is connected through a manifold 60 connected to the upper portion 18 of the tank as shown in FIG. 8. A supply fan 62 is coupled to the manifold to supply a pressurized air flow into the tank above the mattress.

In order to optimally guide the flow of air through the mattress for drying, a suitable barrier 64 is mounted within the tank to define a drying chamber within the wash tank having a first zone on a first side of the barrier and a second zone on a second side of the barrier so as to isolate one or more surfaces of the mattress in communication with the first zone from other surfaces of the mattress in communication with the second zone when the mattress spans an opening in the barrier as shown in FIG. 8. In the illustrated embodiment, the barrier includes a main barrier portion lying coplanar with the lower grate that occupies the opening in the barrier so that the barrier fully surrounds the lower grate and spans outwardly therefrom to the surrounding walls of the tank. The barrier may be adjusted in size or replaced with different barriers of different size so that the open area of the grate upon which the mattress is supported can be sized to match the corresponding dimensions of the mattress. The barrier material prevents the flow of air therethrough so as to isolate the backside surface of the mattress in communication with the second zone below the barrier from the sleeping surface and side surfaces of the mattress in communication with the first zone above the barrier. In this manner, a high pressure first zone is created above the mattress by the supply of air from the supply fan or blower 62 and a low pressure second zone is created below the mattress by the exhaust fan 58 to induce airflow downwardly through the mattress from the top sleeping surface to the backside surface thereof which induces the migration of wash/rinse liquid in the mattress externally of the mattress through the backside surface of the mattress.

The barrier 64 may optionally include a skirt portion (not shown) which fully covers all of the side surfaces of the mattress for blocking the flow of air through the side surfaces of the mattress. In this manner, all airflow from the high pressure zone to the low pressure zone is directed into the mattress through the top sleeping surface and out of the mattress through the backside surface of the bottom of the mattress.

To assist the drying process, and optionally add a degree of sterilization to the drying cycle, a heater 66 is typically mounted in series with the supply ducting in close proximity to the wash tank. Optional heaters include an electrical resistance heating element or a combustion type heater which produces heat by a combustion of a fuel.

Regardless of the particular mechanism used, a typical operation for cleaning a mattress involves initially fully submerging the mattress. During the wash cycle, a pressure applicator is used to apply a cyclical compressive force to the sleeping surface of the mattress while the mattress is supported on the mattress support 34 fully submerged within the tank so as to cause cyclical flushing 70 of the wash liquid inwardly and outwardly of the mattress through one or more surfaces of the mattress in response to each compression of the mattress.

The pressure applicator may involve use of the nozzles to apply pressure using jets of liquid of sufficient pressure to provide some compression of the mattress, and thus some flushing of liquid outwardly through the corresponding surface of the mattress being compressed. Alternatively, or in addition to the use of nozzles, the pressure applicator may include use of opposing upper and lower grates which are displaced relative to one another to cyclically compress the mattress therebetween, again to cause cyclical flushing 70 of the wash liquid inwardly and outwardly of the mattress through one or more surfaces of the mattress upon each compression of the mattress.

In either instance, the pressure applicator is typically operated to apply compression rapidly for quickly expelling and outwardly flushing liquid from the mattress to remove soiling materials at the surface of the mattress. The corresponding release of pressure, for example the return stroke of a reciprocated upper grate, occurs at a slower rate than the application of the initial compressive force so that the return of liquid into the mattress as the mattress is uncompressed is less likely to carry soiling materials deeper into the mattress. The various cycles which may occur while the mattress is submerged include one or more chemical treatments of liquid being flushed through the mattress, one or more wash liquids being flushed through the mattress, and one or more rinse liquids being flushed through the mattress. Between each submerged cycle, the wash tank is typically drained of the corresponding liquid before introduction of the next liquid for the next cycle.

Upon completion of each cycle involving liquid, or optionally only upon the completion of the final liquid cycle, some dewatering of the mattress is preferred before drying begins. This can be accomplished by any of the various techniques described above to compress the mattress using grates or a bladder membrane for example.

As described above, the drying cycle of the mattress can occur within the same wash tank by connection of the suitable supply and exhaust ducts. When the mattress initially begins the drying cycle and remains saturated with liquid so that the pores of the various materials forming the mattress are substantially filled with liquid, the initial application of an air pressure differential between upper and lower zones of the tank is typically sufficient to cause some physical compression of the overall height of the mattress which assists in further squeezing liquid out of the mattress. The air pressure differential urges the water or other liquids within the pores of various materials forming the mattress to migrate in the flow direction from the top side to the bottom side of the mattress and subsequently externally from the mattress. As some of the pores within the mattress become vacated of liquid and air begins to move more freely through the mattress from the top side to the bottom side thereof, the mattress is less prone to remaining compressed by the air pressure differential, and the air flow through the mattress tends to cause more evaporation of liquid within the mattress so that liquid is carried externally of the mattress as a vapour within the passing airflow.

To ensure all surfaces of the mattress are adequately washed and subsequently dried, a suitable mechanism may be provided within the tank to shift or re-position the mattress relative to the mattress support at one or more periodic intervals during the washing and/or drying cycles. In one embodiment, a series of fingers may be mechanically operated to extend upwardly through the lower grate and translate laterally relative to the grate before being withdrawn back through the grate so that the mattress is shifted slightly laterally relative to the grate between different positions. Alternatively, the lower nozzles can be used to uniformly direct jets of liquid upwardly and offset laterally in a common direction with sufficient liquid pressure to lift and laterally shift the mattress relative to the lower grate upon which it is supported.

Turning now more particularly to FIG. 1, the overall cleaning process as illustrated by steps S1 through S27, will now be described in further detail. The process typically begins with collecting a mattress from the customer or receiving a delivered mattress at the cleaning location. Upon initial inspection, if it is determined that no insects are present, the mattress is appropriately labelled and sealed within a suitable plastic bag for subsequent delivery to a cleaning facility deemed to be free of insects. Alternatively, if it is determined that insects are present, for example lice, bedbugs, mites and the like, the mattress is appropriately labelled in an appropriate insect proof bag for delivery to a suitable cleaning facility where other insect bearing mattresses are processed. These mattress undergo additional treatment directed at killing the insects, for example heat or chemical treatments. In either instance, the mattress is removed from the corresponding bag and the bag is discarded upon arrival at the corresponding facility.

In the instance of a single tank cleaning facility, the mattresses are typically initially vacuumed until the surfaces and edges of the mattress are suitably cleaned. Stained areas are identified and small surface treatments may be applied for example chemical treatments and the like. The mattress can then be placed into the wash tank and the tank is filled with treatment liquid or wash liquid. The mattress is fully submerged and the nozzles and/or mechanical means are applied to the mattress for cyclically compressing the mattress and flushing liquid into and out of the mattress through corresponding surfaces of the mattress. After washing for a specified time, the wash liquid is removed from the tank and a similar cycle is performed with rinse liquids. The rinse liquids are then drained from the tank and dewatering of the mattress occurs using some form of compression. An additional disinfecting cycle may be included using steam or ultrasonically applied steam. Drying of the mattress using heated air is then performed with the air being sufficiently heated to provide some further sanitizing. The clean mattress can then be removed and additional sterilizations can be performed including use of ultraviolet germicidal irradiation and/or ozone application to outer surfaces of the mattress. The clean mattress is then sealed and bagged for return to the customer.

In place of a single tank cleaning facility, the various operations may be performed in an automated or semi automated processing line. In this instance, once the mattress is initially removed from suitable packaging upon arrival at the facility, the mattress is placed on a conveyor for guiding to the first step in the process. At the first station, one or more vacuum devices are applied to the various surfaces of the mattress to clean the surface and edges of the mattress. Stained areas may be located using various means, for example use of ultraviolet blacklight or other means known by people of skill in the art. Spot treatment of identified stains can then be performed similarly to the one tank process. Typically, three types of stains are identified, that is protein stains, tannin stains, and grease stains. The appropriate method and chemicals known to be used in the laundry and upholstery cleaning arts can be used for spot treatment.

The conveyor is suitably arranged to guide the mattress into a cleaning solution tank where the nozzles are located, with optional mechanical means as well, to apply cyclical pressure to the various surfaces of the mattress for washing as described above. The mattress is then guided out of the cleaning tank to be dewatered by various means described above.

A separate tank may then be provided for performing a rinsing cycle followed by dewatering again. Disinfection of the mattress using steam can then also be performed at a dedicated station.

A dedicated drying chamber then receives the mattress therein to apply in the air pressure differential to different surfaces of the mattress which have been isolated from one another by a barrier as described above. Subsequent to the drying chamber, the additional treatment steps for sanitizing the mattress prior to bagging the mattress for return to the customer are similar to the steps described above.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A mattress cleaning system for cleaning a mattress comprising a sleeping outer surface for supporting a user thereon, a backside outer surface opposite the sleeping outer surface, and a plurality of side outer surfaces connected between the sleeping outer surface and the backside outer surface about a perimeter of the mattress, the system comprising:

a wash tank arranged to receive the mattress and a wash liquid therein such that the mattress is submerged in the wash liquid for washing the mattress; and a mattress drying system comprising:
a drying chamber;
a barrier supported within the drying chamber to separate the drying chamber into a first zone at a first side of the barrier and a second zone at a second side of the barrier, the barrier including an opening in the barrier arranged to receive the mattress spanning thereacross so as to be arranged to isolate at least one first surface among the outer surfaces of the mattress in communication with the first zone on the first side of the barrier from at least one second surface among the outer surfaces of the mattress in communication with the second zone on the second side of the barrier; and
a blower in communication with at least one of the first zone or the second zone of the drying chamber so as to be arranged to create an air pressure differential between the first zone at the first side of the barrier and the second zone at the second side of the barrier so as to cause migration of wash liquid through the mattress from the at least one first surface of the mattress to the at least one second surface of the mattress.

2. The system according to claim 1 further comprising a press supported within the wash tank including a first pressing surface for engaging the backside surface of the mattress, a second pressing surface for engaging the sleeping surface of the mattress, and a press drive arrangement arranged to displace the second pressing surface relative to the first pressing surface to compress the mattress subsequent to washing of the mattress.

3. The system according to claim 1 wherein the barrier is adapted to isolate the backside outer surface of the mattress from the sleeping outer surface of the mattress.

4. The system according to claim 3 wherein the barrier is substantially coplanar with and surrounds a grate adapted to span the backside of the mattress and support the mattress thereon.

5. The system according to claim 1 wherein the barrier is arranged to cover the side outer surfaces of the mattress.

6. The system according to claim 1 wherein the barrier is adapted to isolate the side outer surfaces of the mattress in communication with the first zone on the first side of the barrier from the backside outer surface and the sleeping outer surface in communication with the second zone on the second side of the barrier.

7. The system according to claim 1 including a controller operatively connected to the blower and adapted to pulse operation of the blower.

8. The system according to claim 1 further comprising:
the drying chamber being at least partly defined within the wash tank;
a mattress support supported within the wash tank, the mattress support having a mattress supporting surface spanning the opening in the barrier so as to be arranged to support the mattress thereon so that the mattress spans across the opening in the barrier when submerged in the wash liquid during a washing cycle and when operating the blower during a drying cycle;
the mattress supporting surface of the mattress support comprising a grate arranged to receive wash fluid circulated therethrough;
a pressure applicator operatively connected to the wash tank so as to be adapted to apply a cyclical compressive force to the sleeping surface of the mattress while the mattress is supported on the mattress support fully submerged within the wash tank so as to cause flushing of the wash liquid outwardly of the mattress;

the blower being in selective communication with the wash tank; and a drain for draining the wash liquid from the wash tank prior to communication of the blower with the wash tank for drying the mattress.

9. The system according to claim 1 further comprising:

a mattress support in the wash tank arranged to receive the mattress supported thereon such that the mattress is fully submerged in the wash liquid in the wash tank; and a pressure applicator adapted to apply a cyclical compressive force to the sleeping surface of the mattress while the mattress is supported on the mattress support fully submerged within the wash tank so as to cause flushing of the wash liquid outwardly of the mattress through at least the sleeping surface of the mattress.

10. The system according to claim 9 wherein the pressure applicator includes at least one jet nozzle adapted to direct a jet of wash liquid onto the sleeping surface of the mattress in the tank.

11. The system according to claim 10 wherein said at least one jet nozzle is supported relative to the tank so as to be arranged to direct the jet of wash liquid non-perpendicularly to the sleeping surface in a sweeping motion displaced across the sleeping surface of the mattress.

12. The system according to claim 9 wherein the pressure applicator includes (i) a grate supported in the wash tank so as to receive the mattress between the mattress support and the grate, the grate being adapted to allow flow of wash liquid therethrough and (ii) a drive arrangement for reciprocating the grate relative to the mattress support between a first position at a first spacing from the mattress support and a second position at a second spacing less than the first spacing from the mattress support for compressing the mattress as the grate is displaced from the first position to the second position.

13. The system according to claim 12 wherein the first spacing and the second spacing are adjustable amounts.

14. The system according to claim 12 wherein the drive arrangement is adapted to displace the grate from the first position to the second position at a greater speed than from the second position to the first position.

15. The system according to claim 9 further comprising a drain for draining the wash liquid from the wash tank prior to communication of the blower with the wash tank for drying the mattress.

16. A method of cleaning a mattress comprising a sleeping outer surface for supporting a user thereon, a backside outer surface opposite the sleeping outer surface, and a plurality of side outer surfaces connected between the sleeping outer surface and the backside outer surface about a perimeter of the mattress, the method comprising:

washing the mattress by submerging the mattress within a wash liquid;

providing a drying chamber having a barrier therein separating the drying chamber into a first zone at a first side of the barrier and a second zone at a second side of the barrier;

supporting the mattress spanning across an opening in the barrier to isolate at least one first surface among of the outer surfaces of the mattress in communication with the first zone on the first side of the barrier from at least one second surface among the outer surfaces of the mattress in communication with the second zone on the second side of the barrier; and using a blower to create an air pressure differential between the first zone at the first side of the barrier and the second zone at the second side of the barrier so as to cause migration of the wash liquid through the mattress from the at least one first surface of the mattress to the at least one second surface of the mattress.

17. The method according to claim 16 including using the blower to create a sufficiently large air pressure differential between the first side and the second side of the barrier to compress the mattress.

18. The method according to claim 16 including submerging the mattress within the wash liquid in a wash tank, and locating the barrier within the wash tank to define the first and second zones of the drying chamber within the wash tank.

19. The method according to claim 16 including applying a positive pressure to the first zone using the blower and applying a vacuum pressure to the second zone using an exhaust fan separate from the blower.

20. The method according to claim 16 including operating the blower in a pulsed manner.

21. The method according to claim 16 further comprising:
(i) supporting the mattress on a first pressing surface spanning the opening in the barrier; and
(ii) prior to using the blower, partly dewatering the mattress by pressing a second pressing surface against the mattress opposite to the first pressing surface to compress the mattress.

\* \* \* \* \*